Figure 1:
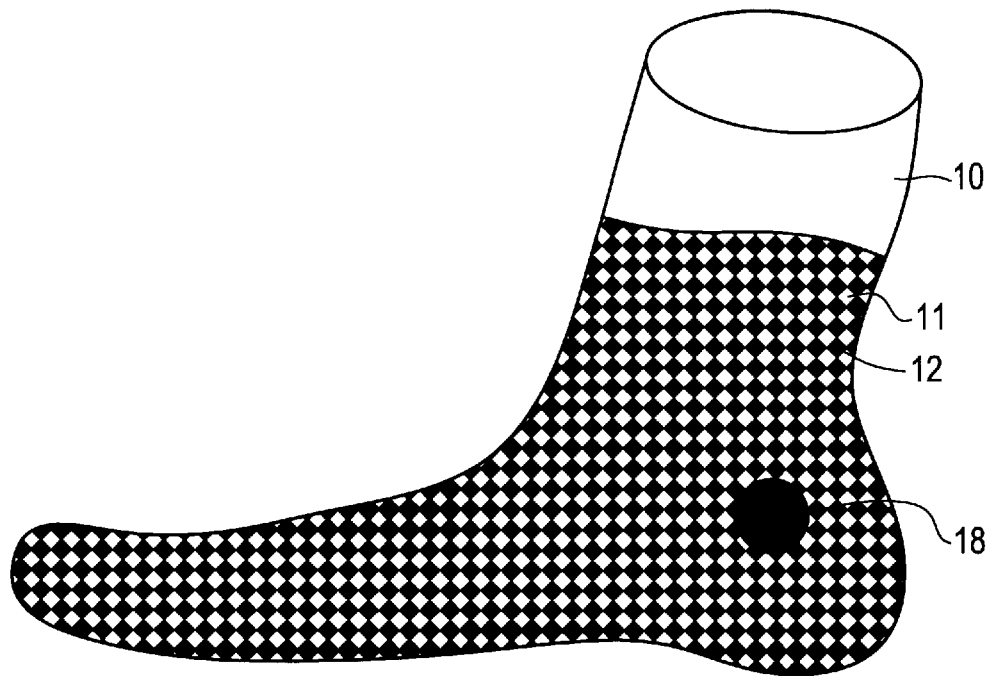

United States Patent

Massen

[11] Patent Number: 5,911,126
[45] Date of Patent: Jun. 8, 1999

[54] METHOD AND ARRANGEMENT FOR DIGITIZED THREE-DIMENSIONAL SENSING OF THE SHAPE OF BODIES OR BODY PARTS

[76] Inventor: Robert Massen, Am Rebberg 29, 78337 Öhningen, Germany

[21] Appl. No.: 08/737,595
[22] PCT Filed: May 22, 1995
[86] PCT No.: PCT/EP95/01934
  § 371 Date: Nov. 22, 1996
  § 102(e) Date: Nov. 22, 1996
[87] PCT Pub. No.: WO95/31934
  PCT Pub. Date: Nov. 30, 1995

[30] Foreign Application Priority Data

May 22, 1994 [DE] Germany .................. 44 17 872

[51] Int. Cl.⁶ .............. G05B 19/42; A61B 5/107
[52] U.S. Cl. ............ 702/153; 364/474.05; 364/474.24; 364/474.25; 382/108; 382/154
[58] Field of Search .............. 364/474.05, 560, 364/474.24, 474.25, 468.04, 468.25; 382/154, 274, 108; 702/153

[56] References Cited

U.S. PATENT DOCUMENTS

| | | | |
|---|---|---|---|
| 4,697,240 | 9/1987 | Cedar et al. | 364/474.02 |
| 4,745,290 | 5/1988 | Frankel et al. | 250/559.17 |
| 4,819,660 | 4/1989 | Smith | 33/515 |
| 4,821,200 | 4/1989 | Oberg | 364/474.24 |
| 4,969,106 | 11/1990 | Vogel et al. | 382/154 |
| 4,982,438 | 1/1991 | Usami et al. | 382/154 |
| 5,127,420 | 7/1992 | Horvath | 600/595 |
| 5,432,703 | 7/1995 | Clynch et al. | 364/474.05 |

FOREIGN PATENT DOCUMENTS

| | | |
|---|---|---|
| 363580 | 10/1981 | Austria . |
| 78310 | 12/1970 | Germany . |
| 3119857 | 12/1982 | Germany . |
| 4232606 | 3/1994 | Germany . |
| 4227571 | 8/1992 | Japan . |

OTHER PUBLICATIONS

F. Carrico, "Rapid Anthropometry for CAD/CAM Design in Prosthetics and Orthotics", RESNA 12th Annual Conference, New Orleans, Louisiana, p. 157, 1989.

Jack L. Lancaster et al., "Evaluation of a Laser Scanner for Shape Sensing BKN Amputees", RESNA 12th Annual Conference, New Orleans, Louisiana, pp. 155–156, 1989.

*Primary Examiner*—John Barlow
*Assistant Examiner*—Hien Vo
*Attorney, Agent, or Firm*—Sixbey, Friedman, Leedom & Ferguson, P.C.; Gerald J. Ferguson, Jr.; Eric J. Robinson

[57] ABSTRACT

For largely automated production of artificial limbs or adapted moldings, digitized three-dimensional image data of the shape of body or body parts are obtained, particularly of human body parts or limbs. The body or body part is covered by a thin, tight-fitting, preferably elastic envelope carrying a high-contrast pattern that is imaged by several cameras cooperating in the manner of stereo cameras having overlapping image areas. The image signals furnished by the cameras are digitized and supplied to a computer that computes the digitized data of the three-dimensional shape by automatic coordination of corresponding patterns in each of the recorded images.

18 Claims, 4 Drawing Sheets

METHOD AND ARRANGEMENT FOR DIGITIZED THREE-DIMENSIONAL SENSING OF THE SHAPE OF BODIES OR BODY PARTS

The invention relates to a method and an arrangement for digitized three-dimensional sensing of the shape of bodies or body parts, particularly human body parts or limbs, for largely automated production of artificial limbs or adapted moldings in which the body or body part together with a high-contrast pattern on the surface thereof is imaged by several cameras cooperating in the manner of stereo cameras having overlapping image areas and in which the digitized data of the three-dimensional shape are obtained by automatical coordination of corresponding patterns recorded in the images by means of a computer.

A method of this kind is known from the East German Patent 78 310 for the purpose of sensing anthropometric data. In this method, by making use of a stereo measuring camera, one or more images are produced from one side of the body of a test person after assuming a specified stance and fixing this by a suitable device, the body surface being previously provided with a shaded or raster structure by an arrangement of structure walls and light sources. The stereo images are evaluated by means of stereo autographs or stereo comparators and the data obtained from the images are evaluated and further processed by automatic electronic processor means.

This method is not well suited for three-dimensionally sensing the shape of bodies or body parts for largely automated production of artificial limbs or adapted moldings. For this purpose namely the body or body part needs to be imaged from various sides in as short a time as possible, preferably simultaneously, since the patient must not move during optical sensing. Meeting this requirement is particularly opposed by the structured illumination by means of structure walls and light sources which cannot be done at the same time for the various imaging directions. Since optical sensing needs to be done also independently of skin type and possible hirsuteness, complicated and time-consuming preparatory measures are needed, such as applying a reflective make-up or even depilation by shaving.

Furthermore, hygiene problems are involved. Since parts of the imaging equipment successively come into contact with naked body parts of various patients, it is necessary to configure these parts so that they can be regularly disinfected. Permitting disinfection necessitates the use of expensive materials which just like the time needed for disinfection increases the costs involved.

It is known, on the other hand, to sense the shape of body parts or limbs three-dimensionally by means of active laser scanners. In a method known from the PCT publication WO 92/08175 a single line of light is projected by means of a laser source on the body part covered by a thin, elastic envelope, this light line tracking the profile of the body part. By triangulation with the aid of an optical sensor the three-dimensional coordinates of the individual points of this profile line are determined. This procedure is repeated for further profile lines, a rotary table carrying the laser scanner being rotated each time by a small angle until in conclusion the body part has been completely sensed. In this known system it is also provided for that critical locations of the body part are characterized by markings on the envelope which do not reflect the laser light. These systems operating with active laser scanners are, however, as compared to photogrammetric systems employing passive stero cameras, highly expensive. Furthermore, there is the problem that even in the case of fast-working systems totally sensing a body part three-dimensionally takes up roughly 10 to 15 seconds in which the body part must not be moved.

As compared to this, the object of the invention is to provide a passive photogrammetric multi-camera method which permits, at little expense, very fast three-dimensional sensing of the shape of a body or body part, eliminating the need for preparatory measures concerning the body or body part to be imaged and having no need for disinfection whilst meeting the hygiene requirements.

On the basis of a method of the kind as cited at the outset this object is achieved according to the invention in that the body or body part is covered prior to imaging with a thin, tight-fitting envelope carrying the high-contrast pattern.

In the case of the method according to the invention this thin, tight-fitting envelope satisfies several functions:

1. It carries the pattern necessary for the photogrammetric evaluation, this pattern covering the whole of the surface of the body or body part to be imaged without the necessity of complicated projections. As a result of this, it is now possible, in particular, to take the images from various directions and even from all directions necessary at the same time, as long as a corresponding number of cameras is provided. Despite this, the expense involved is relatively slight, since electronic image sensors can be employed as the cameras which are available as mass-production items at low cost. For the lighting a simple and cheap diffused light source is sufficient.

2. Due to using the envelope with the pattern provided thereon optical conditions are ensured which are always the same irrespective of the surface quality of the body or body part to be imaged, this thus eliminating the need for tedious preparations such as make-up or depilation.

3. Since the body or body part covered by the envelope does not come into direct contact with parts of the imaging equipment, total hygiene satisfaction is always assured without any disinfection being needed, this applying in particular when the envelope is fabricated as a cheap disposable article used once only.

4. The envelope also hides unsightly wounds or mutilations of amputated body parts or limbs, as a result of which the psychic stress on both the patient and on the imaging personnel is alleviated.

Advantageous aspects and further embodiments of the method according to the invention as well as an arrangement for implementing the method are characterized in the sub-claims.

Figure 2:
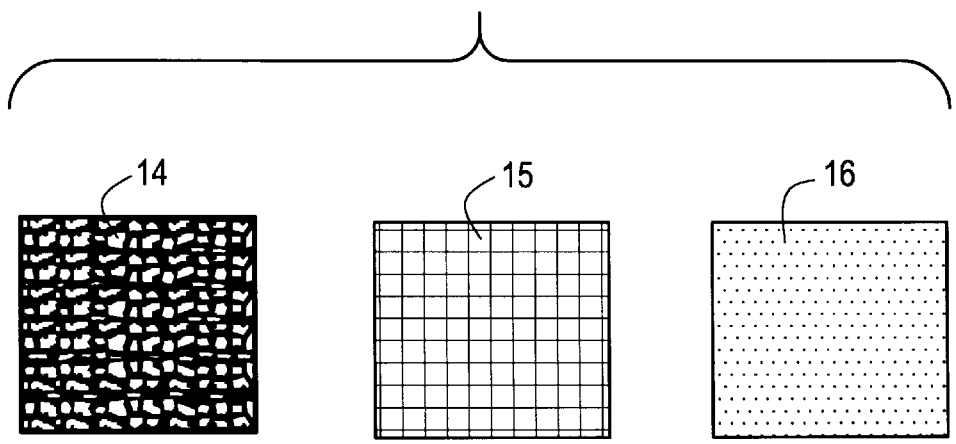
Figure 3:
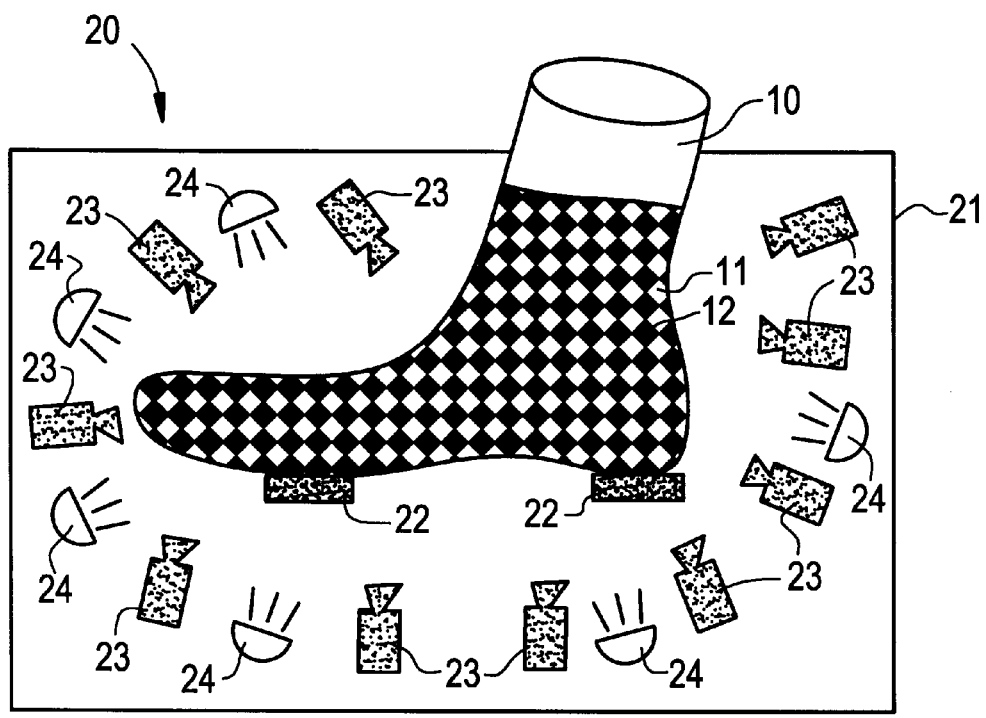
Figure 4:
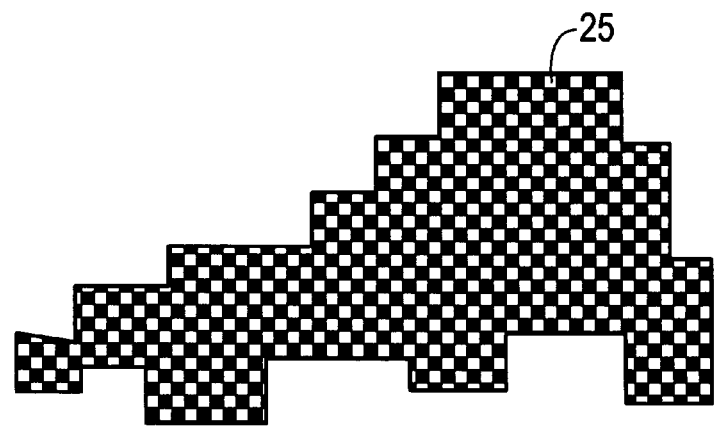
Figure 5:
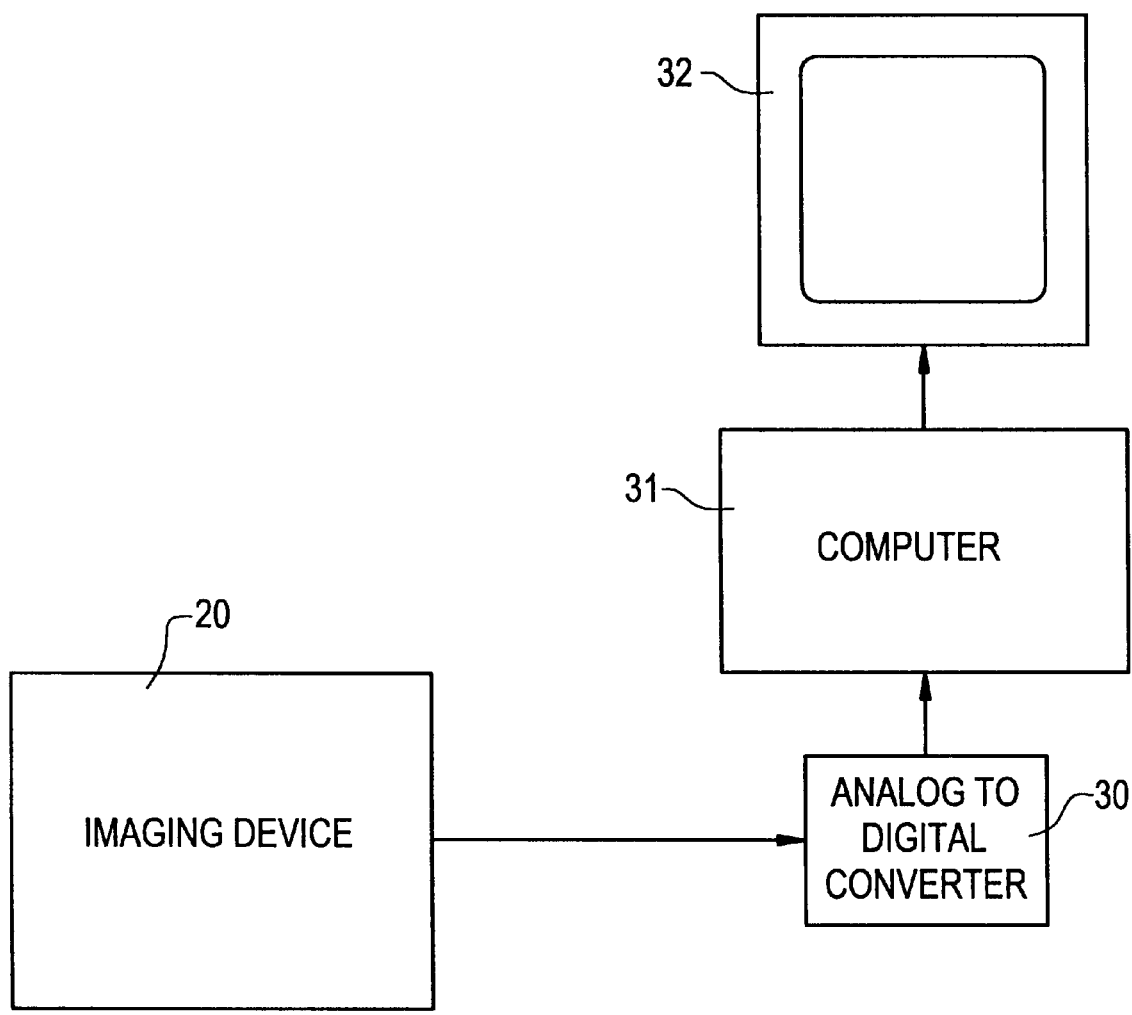
Figure 6:
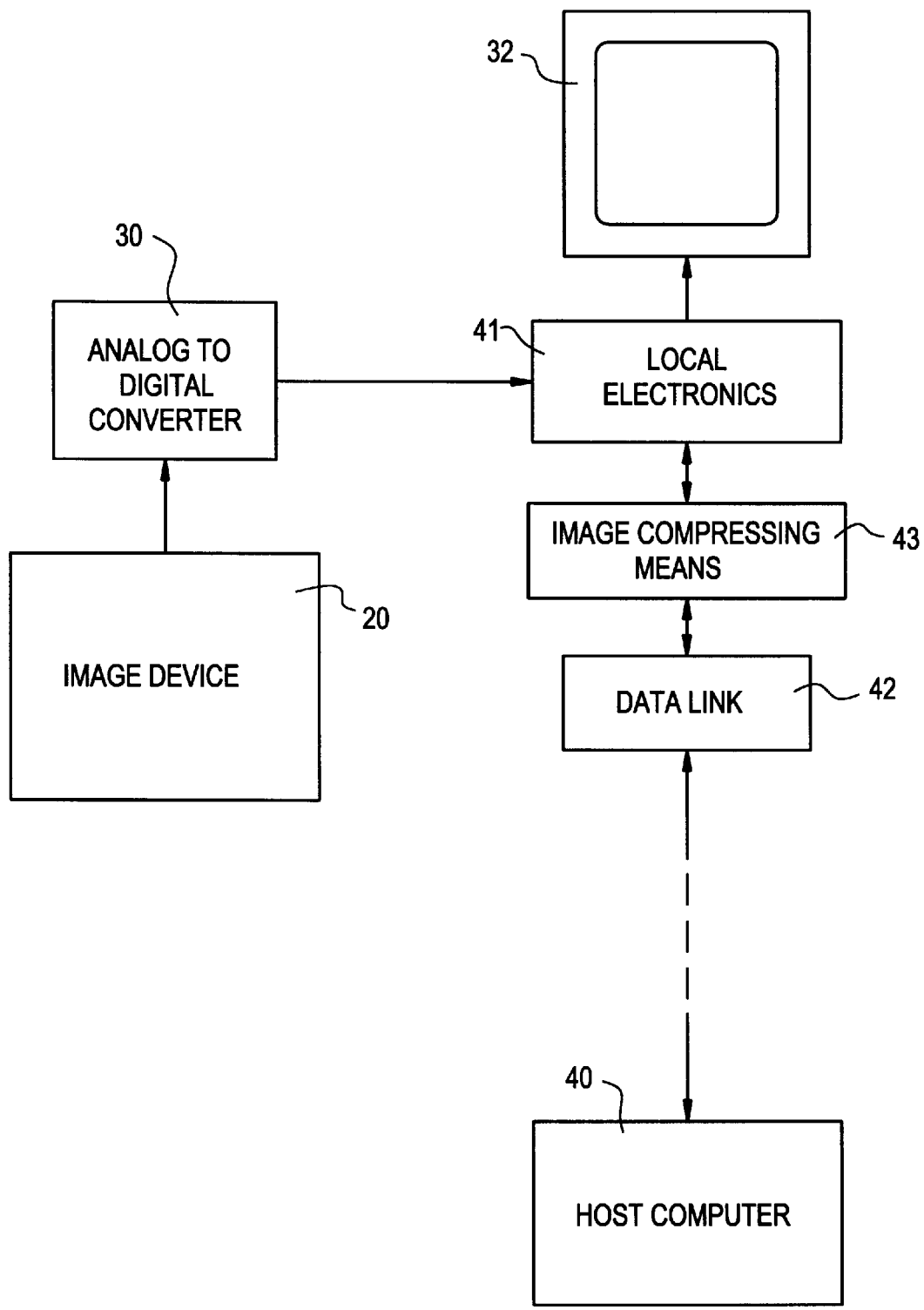

Further features and advantages of the invention will be appreciated from the following description of an example embodiment with reference to the drawings, in which:

FIG. 1 shows, as an example of a body part, a foot provided with an envelope, the shape of which is to be sensed three-dimensionally, FIG. 2 shows various examples of patterns which may be provided on the envelope, FIG. 3 schematically represents the imaging means, FIG. 4 shows a calibration body for calibrating the system, FIG. 5 is a block schematic of the sensing system as a whole, and FIG. 6 is a block schematic of a modified embodiment of the sensing system.

Sensing the shape of a body or body part three-dimensionally using several cameras in a stereo arrangement requires overlapping image areas to be sensed in each case by at least two cameras. Identical structures in the common image region are, due to imaging being done in differing directions, imaged in the respective imaging plane of each camera at differing positions. The offset of these structures between the images recorded by two cameras in each case is proportional to the distance from the two cameras and may be converted into XYZ coordinates, when the position of the cameras is known three-dimensionally. The stereophotography may also be expanded to more than two cameras and even permits, in particular, also specific results when no purely random structures are visible in the common image areas. The mathematical and/or photogrammetric basics of stereophotography as well as the calibration of such arrangements are known to the person skilled in the art and thus need not be further explained in this context.

As an example of a body part, the shape of which is to be sensed three-dimensionally, a foot 10 is represented in FIG. 1. The foot 10 is covered by a thin, tight-fitting, preferably elastic envelope 11 which for reasons of hygiene is used once only and in the case of the foot 10 takes the form of a sock. By using the envelope 11 all make-up and depilation procedures are eliminated, as otherwise necessary when dark or hairy skin regions are to be optically sensed three-dimensionally. In addition, employing the hygienic disposal sock prevents naked body parts coming into contact with mounting fixtures of the imaging device which would need disinfection before each imaging procedure. Since numerous patients with foot problems also suffer from skin diseases such as rashes, inflamed and tender irritations, etc., hygienic screening is particularly important.

The envelope 11 consists preferably of a fine-gauge woven or knitted elastic textile material, for example, a so-called stretch fabric. It may, however, also be made of a film of rubber or an elastomer plastics material. Furthermore, the envelope may be formed by a shrink film which shrinks into a close fit about the body or body part when heated by the application of hot air or spray-application of a chemical reagent. In conclusion, it is also possible to form the envelope by spray application of a coating material directly on the body or body part.

The surface of the envelope 11 is light and provided with a high-contrast pattern 12 suitable for stereo evaluation. This pattern may be of a random, irregular texture which in stereo evaluation permits an explicit correlative matching, or it may be a regular and periodic pattern, as shown in FIG. 1, which by evaluation by more than two camera images, comprising a common overlapping region, results in explicit surface coordinates, despite the periodic structure. Such suitable patterns are known to the person skilled in the art of photogrammetry. In FIG. 2 an irregular pattern 14, a cross-hatched pattern 15 and a dotted pattern 16 are shown as examples, all of which are suitable for this purpose. The pattern 12 may be printed on the material of the envelope 11 or applied by other means known to the person skilled in the art, for instance, by spray-application. in the case of a woven or knitted envelope the pattern may also be included in the weave or knit.

On the envelope 11 provided with the pattern 12 additional, certain prominent locations of the foot may be marked with the aid of a scriber, e.g. the position of the ankle by a marking 18 so that in later evaluation of the recorded images an assignment of surface coordinates to significant points, lines or regions of the foot is possible. Such markings may be easily recognized in the camera images by known methods of image processing and distinguished from the patterns intended for stereo evaluation. Also, colored markings and patterns may be used, of course, when the cameras employed are color-sensitive.

It is schematically represented in FIG. 3 how sensing the shape of the foot 10 three-dimensionally is done in an imaging device. The imaging device 20 has a box-shaped housing 21 into which the foot 10 is introduced from above. Mounts 22 maintain the foot 10 in a predetermined position. In the interior of the housing 21 several cameras 23 are located about the foot 10 so that they can totally image the complete foot in all directions and the image areas overlap partly in pairs or groups such that at least two cameras each sense a common image region. Furthermore, lamps 24 are included in the housing 21 which provide diffused illumination of the complete foot. Instead of the plurality of concentrated light sources, as depicted in FIG. 3, a few elongated light sources, such as fluorescent tubes, may be employed for diffused illumination of the foot. In any case the means of illumination are simple and cheap, there being no need for costly structured illumination, due to using the pattern 12 provided on the envelope 11.

The cameras 23 are electronic image sensors which convert the recorded images into electrical image signals. For this purpose semiconductor cameras are used preferably which as articles of mass production are available at very moderate cost so that also using numerous cameras still represents a cost-effective solution. Particularly the development of the single-chip camera permits employment of even a large number of cameras at low system costs. The fact that no moved parts, such as rotary tables or the like are need in the imaging device is a particular cost-saving factor.

Preferably, imaging the complete foot is done by all cameras simultaneously, so that only a very brief imaging time is needed and thus the time of no movement is conveniently short for the patient.

For calibrating the system a calibrating body 25, as represented schematically in FIG. 4, correspondingly positioned in the imaging device 20 is recorded and gauged by all cameras 23. The calibrating body 25 has a known geometry and carries on its surface a pattern of the kind of the pattern 12 applied to the envelope 11. Due to the fact that all planes, markings and positions are known, all of the measured coordinates can be translated into a machine coordinate system which is given by the matching position of the calibrating body. Conversion into a object-related system of coordinates, which is defined e.g. by markings applied to the envelope, is thus possible at any time.

Classic methods of photogrammetry also include those for precise three-dimensional gauging with the aid of several cameras, the positions of which are not known three-dimensionally, but which each sense a certain number of identical markings. These methods, too, may also find application, the high-contrast pattern 12 then being used as the markings.

FIG. 5 shows the overall configuration of the sensing system. The image signals furnished by the cameras 23 in the imaging device 20, if not already existing in digital form, are digitized in an analog to digital converter 30 and supplied to a computer 31 which is connected to a monitor 32 permitting a visual check of the individual images. The computer 31 carries out the photogrammetric computations and generates a 3D data set which again can be displayed for checking on the monitor 32.

FIG. 6 shows a modified embodiment of the sensing system in which for cost savings the programmetric computation is assigned to a host computer 40. The local electronics 41 at the sensing site then merely serve to reproduce the individual camera images on the monitor 32 and for transmitting the generated raw image data to the host computer 40 by means of a suitable data link 42. If need be, the image signals may be compressed in am image compression means 43 prior to transfer. The image signals evaluated in the host computer 40 can be transferred back to the local electronics 41 for checking and reproduced as images on the monitor 32.

In any case the 3D data computed by the computer 31 or host computer 40 may be put to use for automated fabrication of a shoe lath, bedding or foot molding.

Gauging feet, as shown, is but one example of an application. In gauging other limbs and parts of the body the problems as to the technical, hygiene and cost-effective aspects, as discussed, also occur which can be overcome by using a hygienic, flexible disposable envelope having a light surface contrastingly patterned, thus permitting speedy and cost-effective passive optical sensing of the shape three-dimensionally by a multiple camera arrangement. Further example are e.g. gauging the buttocks for the production of adapted seat buckets, gauging back parts for the production of adapted seat backs, gauging arm and leg stumps for the production of artificial limbs, and so on. The range of application thus exceeds also that of purely medical applications and is always appropriate when shapes adapted to that of a body individually need to be produced.

The method described may, of course, also be translated to the digitized sensing of object shapes three-dimensionally which are not parts of the human body, such as design models, prototype designs and the like.

I claim:

1. A method for digitized three-dimensional sensing of the shape of bodies or body parts, particularly human body parts or limbs, for largely automated production of artificial limbs or adapted body parts, said method comprising the steps of:

covering said body or body part with a thin, tight-fitting envelope carrying a high-contrast pattern;

recovering images of the covered body or body part with a plurality of cameras cooperating in the manner of stereo cameras having overlapping image areas; and obtaining, by computerized automatic coordination of the corresponding high-contrast pattern recorded in each of the images taken by said cameras, digitized data representative of three-dimensional shape.

2. The method as set forth in claim 1, wherein said envelope has a light surface on which said high-contrast pattern is applied in a darker color.

3. The method as set forth in claim 1 or 2, wherein said high-contrast pattern is random.

4. The method as set forth in claim 1 or 2, wherein said high-contrast pattern is periodic.

5. The method as set forth in claim 1, wherein said envelope is elastic.

6. The method as set forth in claim 5, wherein said envelope consists of rubber or an elastomer plastics material.

7. The method as set forth in claim 1, wherein said envelope consists of woven or knitted textile material.

8. The method as set forth in claim 7, wherein said pattern is woven or knitted in said envelope.

9. The method as set forth in claim 1, wherein said pattern is printed on said envelope.

10. The method as set forth in claim 1, wherein after application of said envelope and prior to imaging the envelope provided with said high-contrast pattern, selected positions of said body or body part are provided manually with markings and these markings are recognized in said images by image processing methods and employed as assistance in assigning three-dimensional surface coordinates to said makings of said body or body part.

11. The method as set forth in claim 1, wherein said cameras comprise electronic image sensors outputting electrical image signals representing said images, said image signals furnished by said image sensors being digitized and passed on to a computer wherein three-dimensional coordinates of the surface of said body or body part are computed according to known photogrammetric methods.

12. The method as set forth in claim 11, wherein said image signals are transmitted by a data link from local electronics to a host computer for photogrammetric evaluation.

13. The method as set forth in claim 12, wherein for checking for correct digitization and evaluation said digitized and evaluated image signals are transferred back from said host computer to said local electronics for display.

14. The method as set forth in claim 1, wherein for receiving human body parts or limbs, said envelopes are designed and employed as disposable articles.

15. An arrangement for implementing the method as set forth in one of claims 1, 2, 5, 6, 7, 8, 9, 10, 11, 12, 13, or 14, comprising an imaging device for imaging said body or body part covered by said thin, tight-fitting envelope, containing illumination means for diffused illumination of said body or body part, and a plurality of electronic image sensors having image areas overlapping in pairs or groupwise, and comprising a computer to which said image signals of all image sensors are transferred.

16. The arrangement as set forth in claim 15, wherein said patterns carried by said thin, tight-fitting elastic envelope contrast in color, and said electronic image sensors are color-sensitive image sensors.

17. The arrangement as set forth in claim 15, wherein said image sensors in said imaging device are arranged so that they sense the complete surface of the body or body part to be imaged and that imaging is done by all imaging sensors simultaneously.

18. The arrangement as set forth in claim 16, wherein said image sensors in said imaging device are arranged so that they sense the complete surface of the body or body part to be imaged and that imaging is done by all imaging sensors simultaneously.

* * * * *